US011154713B2

United States Patent
Stone et al.

(10) Patent No.: US 11,154,713 B2
(45) Date of Patent: Oct. 26, 2021

(54) ELECTRODE STRUCTURE FOR IMPLANTABLE MEDICAL LEADS

(71) Applicant: Medtronic, Inc., Minneapolis, MN (US)

(72) Inventors: Richard T. Stone, Minneapolis, MN (US); Robert J. Davies, Mounds View, MN (US); Seth M. Humphrys, Golden Valley, MN (US); Darren A. Janzig, Center City, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/348,661

(22) PCT Filed: Oct. 13, 2017

(86) PCT No.: PCT/US2017/056481
§ 371 (c)(1),
(2) Date: May 9, 2019

(87) PCT Pub. No.: WO2018/089168
PCT Pub. Date: May 17, 2018

(65) Prior Publication Data
US 2019/0321630 A1 Oct. 24, 2019

Related U.S. Application Data

(60) Provisional application No. 62/420,922, filed on Nov. 11, 2016.

(51) Int. Cl.
*A61N 1/36* (2006.01)
*A61N 1/05* (2006.01)
(52) U.S. Cl.
CPC ...... *A61N 1/3605* (2013.01); *A61B 2562/125* (2013.01); *A61N 1/0534* (2013.01)

(58) Field of Classification Search
CPC ...... A61N 1/05; A61N 1/0534; A61N 1/0551; A61N 1/0531; A61N 1/0553;
(Continued)

(56) References Cited

U.S. PATENT DOCUMENTS

| 4,224,499 A | 9/1980 | Jones |
| 5,097,835 A | 3/1992 | Putz |

(Continued)

FOREIGN PATENT DOCUMENTS

| WO | 2011/000791 A1 | 1/2011 |
| WO | 2013/117547 A1 | 8/2013 |

OTHER PUBLICATIONS

Loeb et al., "Toward the ultimate metal microelectrode," Elsevier, Journal of Neuroscience Methods, vol. 63, Jul. 29, 1995, 9 pp.

(Continued)

*Primary Examiner* — Jon Eric C Morales
(74) *Attorney, Agent, or Firm* — Shumaker & Sieffert, P.A.

(57) ABSTRACT

An implantable segmented electrode structure may be configured to conduct electrical signals between elongated conductors of an implantable medical lead and respective portions of tissue of a patient. The implantable medical lead may extend from an implantable medical device that is implanted within the patient. The segmented electrode structure includes a plurality of separate electrode surfaces. The electrode surfaces are at a plurality of different axial positions and angular positions within the implantable segmented electrode structure. The segmented electrode structure additionally includes a plurality of prongs. The prongs extend axially from a proximal end of the segmented electrode structure through the segmented electrode structure. Each prong may electrically connect to one of the electrode surfaces. The prongs may terminate distally at respective (Continued)

electrode surfaces. Each prong may be configured to electrically connect to one of the elongated conductors.

14 Claims, 11 Drawing Sheets

(58) Field of Classification Search
CPC .............. A61B 2562/227; A61B 5/042; A61B 2562/222; A61B 5/6867
See application file for complete search history.

(56) References Cited

U.S. PATENT DOCUMENTS

| | | |
|---|---|---|
| 5,269,056 A | 12/1993 | Yang et al. |
| 6,697,675 B1 | 2/2004 | Safarevich et al. |
| 7,047,081 B2 | 5/2006 | Kuzma |
| 7,168,165 B2 | 1/2007 | Calzada et al. |
| 7,822,482 B2 | 10/2010 | Gerber |
| 8,214,054 B2 | 7/2012 | Barker |
| 8,670,828 B2 | 3/2014 | Hall et al. |
| 8,676,343 B2 | 3/2014 | Bloemer et al. |
| 8,788,064 B2 | 7/2014 | Mercanzini et al. |
| 9,248,275 B2 | 2/2016 | Digiore et al. |
| 2002/0198446 A1 | 12/2002 | Hill et al. |
| 2010/0269338 A1 | 10/2010 | Dye |
| 2011/0056076 A1 | 3/2011 | Hegland et al. |
| 2011/0077699 A1 | 3/2011 | Swanson et al. |
| 2011/0245887 A1 | 10/2011 | Klardie et al. |
| 2014/0123484 A1 | 5/2014 | Digiore et al. |
| 2014/0316502 A1 | 10/2014 | Seeley |

OTHER PUBLICATIONS

International Search Report and Written Opinion of International Application No. PCT/US2017/056481, dated Jan. 18, 2018, 10 pp.
International Preliminary Report on Patentability from International Application No. PCT/US2017/056481, dated May 14, 2019, 7 pp.

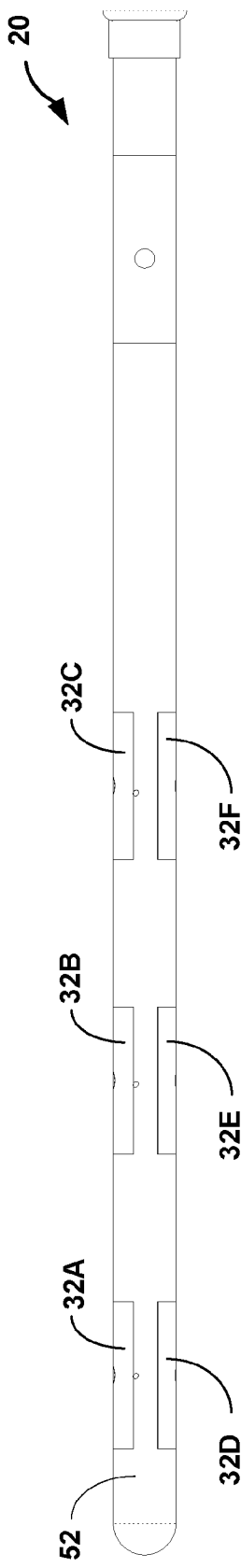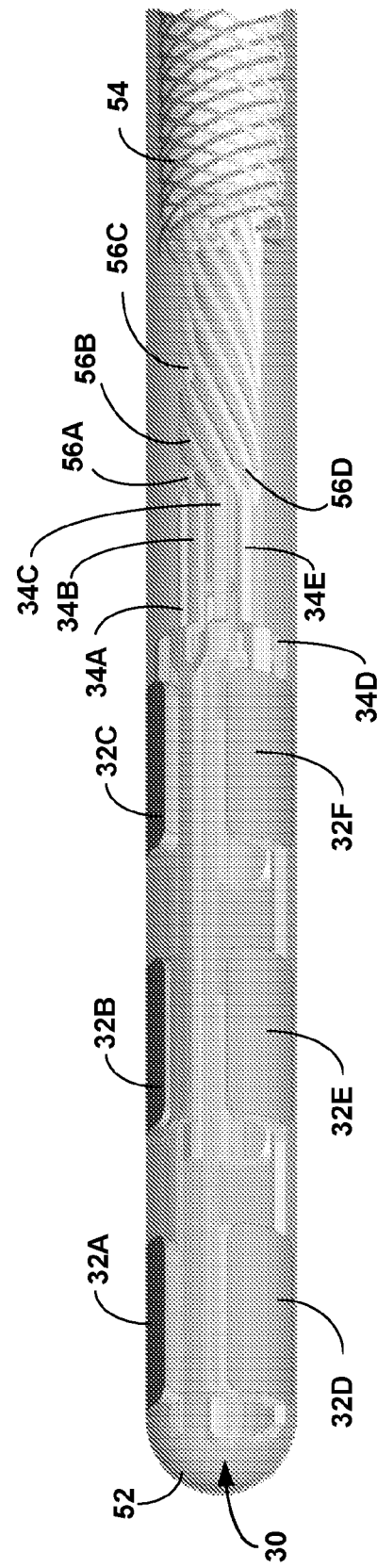
FIG. 3A
FIG. 3B

ELECTRODE STRUCTURE FOR IMPLANTABLE MEDICAL LEADS

This application is a U.S. National Stage entry under 35 U.S.C. § 371 of International Application No. PCT/US2017/056481, filed Oct. 13, 2017, which claims the benefit of U.S. Provisional Application No. 62/420,922, filed on Nov. 11, 2016. The entire contents of each of these applications is incorporated herein by reference.

TECHNICAL FIELD

The disclosure relates generally to implantable medical devices and, in particular, to implantable medical leads configured to conduct electrical signals.

BACKGROUND

The medical device industry has generated a number of implantable medical devices that treat a plethora of medical ailments. Examples of implantable medical devices include pacemakers, defibrillators, and therapeutic substance delivery pumps. Some implantable medical devices deliver electrical stimulation to provide therapy for various medical conditions. For example, chronic pain, tremors, Parkinson's disease, epilepsy, urinary or fecal incontinence, sexual dysfunction, obesity, or gastroparesis have all been treated with implantable medical devices that provide electrical stimulation.

One variety of implantable medical devices is neurostimulators. A neurostimulators may provide electrical stimulation, or "neurostimulation therapy," to the nervous system of a patient. This neurostimulation therapy is often delivered in the form of electrical pulses. An implantable neurostimulator may deliver these electrical pulses using a set of leads. The leads may include electrodes that are positioned near target tissues of the brain, the spinal cord, pelvic nerves, peripheral nerves, or the stomach of a patient, for example. From these different target issues, leads may provide stimulation for different therapeutic applications, such as deep brain stimulation (DBS), spinal cord stimulation (SCS), pelvic stimulation, gastric stimulation, or peripheral nerve stimulation. Implantable medical devices configured to deliver electrical stimulation may alternatively be used for muscle stimulation. For example, an electrical stimulator may provide functional electrical stimulation (FES) to promote muscle movement or prevent atrophy of muscles.

Implantable medical devices may be configured to deliver electrical stimulation via electrodes configured upon the distal end of a lead. Electrodes may be configured on the distal end of a lead in numerous fashions. For example, leads may be cylindrical in shape and include ring electrodes or segmented electrodes. Cylindrical leads with ring or segmented electrodes may be implanted surgically or percutaneously. The electrodes may be electrically connected to a set of elongated conductors. The elongated conductors may be electrically connected to circuitry within the implanted neurostimulator.

SUMMARY

This disclosure includes techniques for the design, manufacture, and use of implantable segmented electrode structures including a plurality of electrode surfaces connected to a plurality of prongs. An implantable segmented electrode structure may be configured to conduct electrical signals between elongated conductors of an implantable medical lead and respective portions of tissue of a patient. The implantable medical lead may extend from an implantable medical device that is implanted within the patient. The segmented electrode structure includes a plurality of separate electrode surfaces. The electrode surfaces are at a plurality of different axial positions and angular positions within the implantable segmented electrode structure. The segmented electrode structure additionally includes a plurality of prongs. The prongs extend axially from a proximal end of the segmented electrode structure through the segmented electrode structure. Each prong may electrically connect to one of the electrode surfaces. The prongs may terminate distally at respective electrode surfaces. Each prong may be configured to electrically connect to one of the elongated conductors.

In some examples, the segmented electrode structure is made from a solid segment of conductive material. The solid segment is machined into an intermediate structure. The intermediate structure is hollow and cylindrical. The intermediate structure defines a longitudinal axis. A distal portion of the intermediate structure includes an outer surface at a first radius from the longitudinal axis. The distal portion further has a plurality of raised surfaces at a second radius from the longitudinal axis. The second radius is greater than the first radius. The intermediate structure is laser cut into the segmented electrode structure. In some examples, the intermediate structure may be laser cut into the segmented electrode structure such that the raised surfaces become the electrode surfaces and the outer surfaces is cut into the axially extending prongs.

In some examples, the plurality of prongs may terminate at a terminal plane at the proximal end of the segmented electrode structure. The terminal plane may be perpendicular to the segmented electrode structure. The plurality of prongs may terminate in a circular arrangement on the terminal plane. The circular arrangement may be centered on the longitudinal axis. The circular arrangement may have a first radius that is less than the second radial distance. The proximal end of the plurality of prongs may be configured to receive a distal version of an elongated conductor hub. The elongated conductor hub may arrange each of the elongated conductors to terminate near respective prongs. The elongated conductor hub may arrange the elongated conductors with helical channels that are defined by helical splines. Elongated conductors may be welded to respective prongs with relatively little elongated conductor manual manipulation upon the prongs receiving the elongated conductor hub.

In some examples, the segmented electrode structure includes a plurality of tabs. Tabs may interconnect aspects of the segmented electrode structure to maintain structural integrity of the segmented electrode structure during the fabrication process. Specifically, tabs may connect a prong and/or electrode surface to circumferentially adjacent prongs and/or electrode surfaces. Tabs may be removed in conjunction with an overmolding procedure to achieve electrical isolation.

The disclosure includes an implantable medical lead. The implantable medical lead comprises the implantable segmented electrode structure described herein. A plurality of elongated conductors of the lead are configured to conduct electrical signals between a medical device and tissue of a patient. The electrical signals are delivered to the tissue of the patent via the electrode surfaces of the segmented electrode structure.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

FIGS. 3A and 3B are perspective diagrams illustrating an example configuration of a distal end of an implantable medical lead.

DETAILED DESCRIPTION

The features and techniques described herein are useful in types of medical device systems, which include implantable medical leads and implantable medical devices. For example, the features and techniques described herein may be used in systems with implantable electrical stimulation leads and implantable medical devices that deliver electrical stimulation therapy to a patient's brain (e.g., DBS). In another example, the features and techniques described herein may be used in systems with medical devices that deliver electrical stimulation therapy to a patient's heart (e.g., pacemakers, and pacemaker-cardioverter-defibrillators). As other examples, the features and techniques described herein may be embodied in systems that deliver other types of electrical stimulation therapy (e.g., spinal cord stimulation, peripheral nerve stimulation, pelvic nerve stimulation, gastric nerve stimulation or vagal nerve stimulation), stimulation of at least one muscle or muscle groups, stimulation of at least one organ such as gastric system stimulation, stimulation concomitant to gene therapy, and, in general, stimulation of any tissue of a patient.

The conventional manufacturing of conventional leads often includes a difficult and labor-intensive step of manually manipulating elongated conductors to get near respective electrodes so that elongated conductors can be manually welded to respective electrodes. This conventional step often includes uncoiling and straightening elongated conductors at a distal end. This conventional step may also include arduously working to electrically connect (e.g., weld) numerous conductors to numerous electrodes in a small space. Conventionally, the distal end of a lead may include numerous elongated conductors bunched together very close to the longitudinal axis of the lead, making electrical isolation difficult to attain due to the proximity of the conductors.

Aspects of the disclosure relate to an implantable segmented electrode structure that electrically connects electrode surfaces to prongs that terminate adjacent to elongated conductors. Providing a structure that aligns prongs that are electrically connected to electrode surfaces adjacent to elongated conductors may provide cycle time benefits within the manufacturing process. The implantable segmented electrode structure may be predominantly hollow. The predominantly hollow nature of the implantable segmented electrode may provide performance benefits to the implantable segmented electrode structure by reducing electrical interference. The implantable segmented electrode structure may be machined and/or laser cut out of a single segment of an electrically conductive material. Producing the implantable segmented electrode structure from a single segment of an electrically conductive material may provide manufacturing benefits such as reducing cost and scrap rate.

Figure 1A:
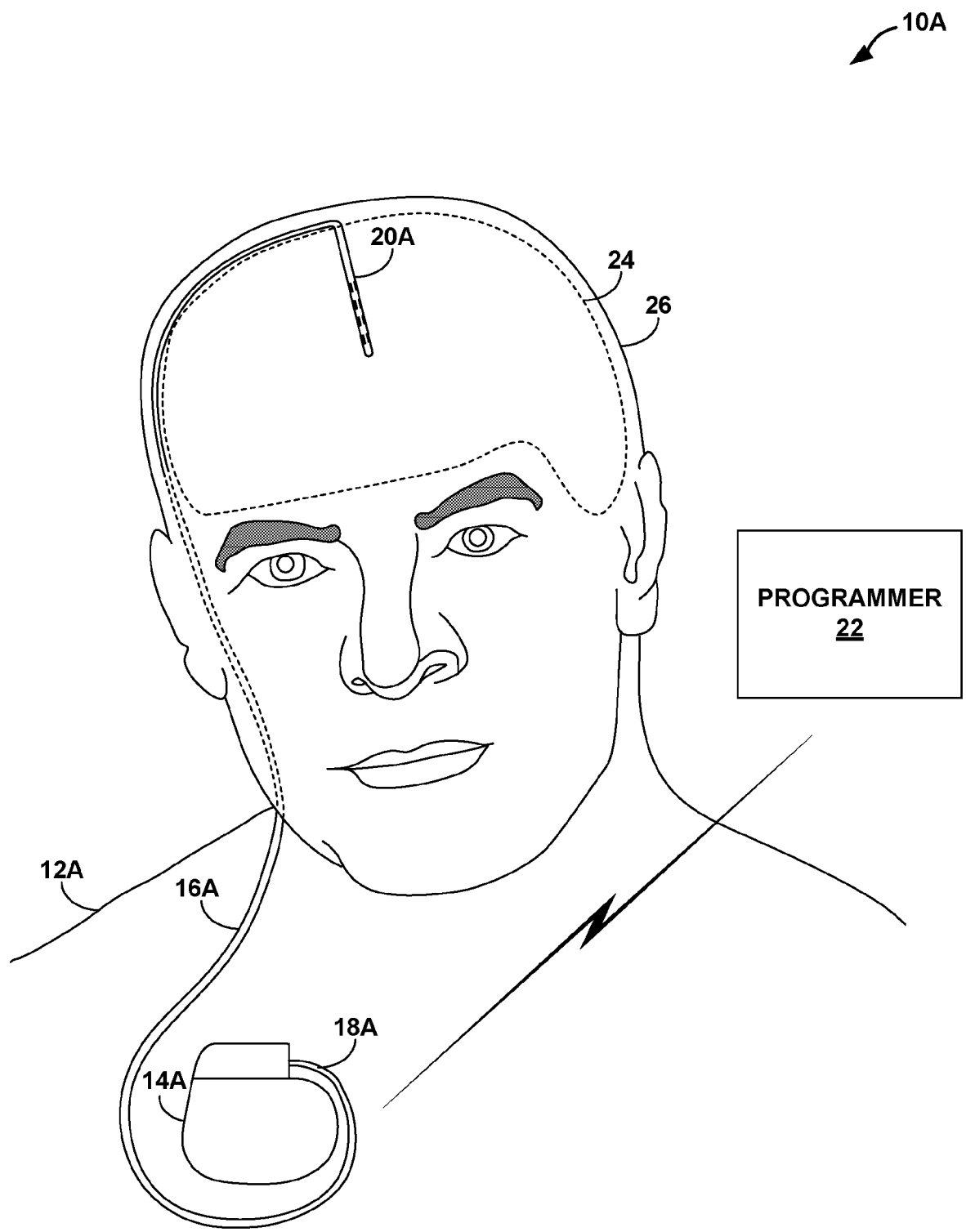
FIGS. 1A and 1B are conceptual diagrams illustrating example medical device systems that include implantable medical devices coupled to implantable medical leads.
Figure 1B:
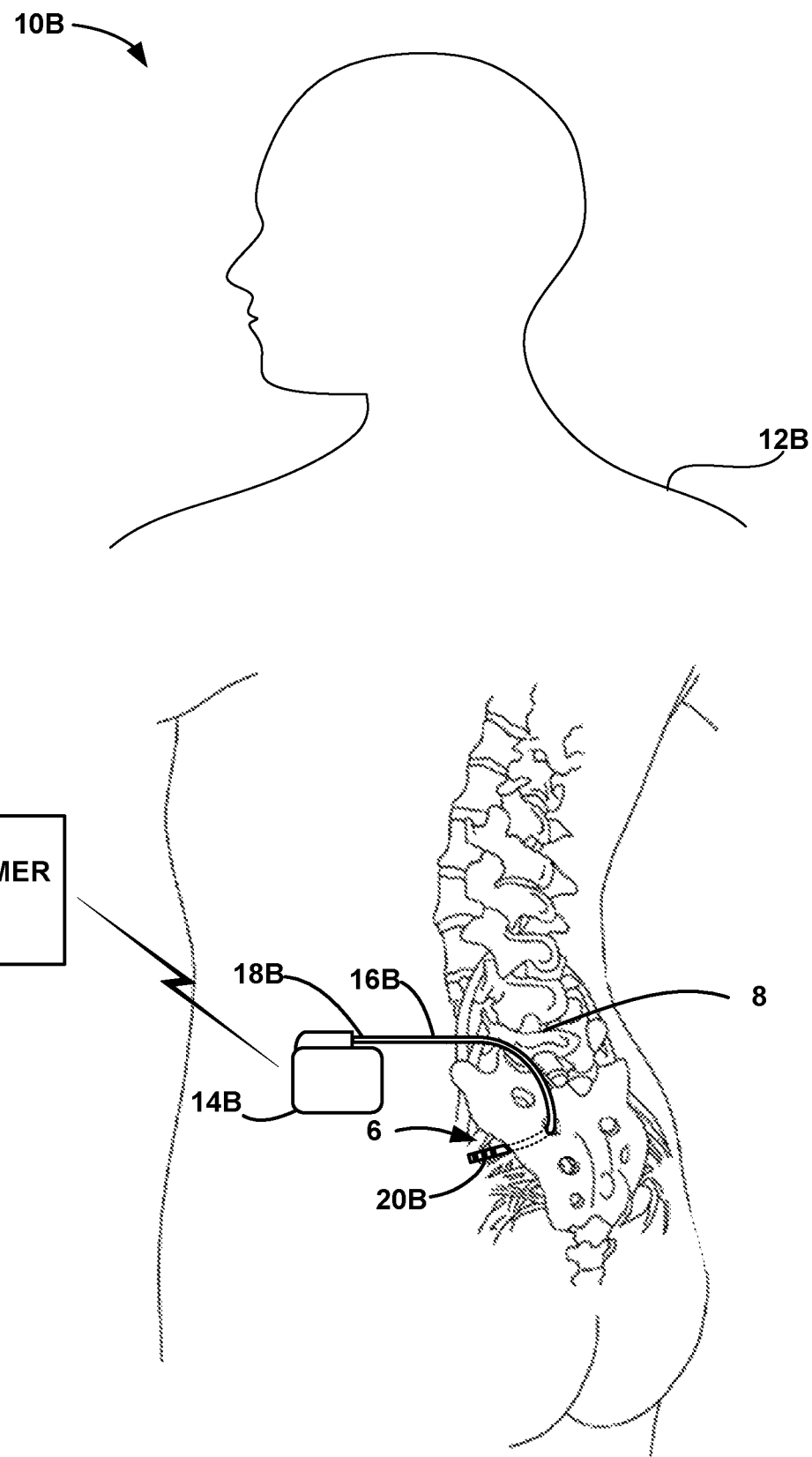

FIGS. 1A and 1B are conceptual diagrams illustrating example medical device systems 10A and 10B (collectively, "medical device systems 10") that include implantable medical devices coupled to implantable medical leads. In the example of FIG. 1A, medical system 10A includes an IMD 14A configured to deliver therapy to and/or sensing physiological signals from brain 24 of patient 12A through lead 16A. More particularly, IMD 14A may deliver electrical stimulation and sense electrical signals via electrodes at distal end 20A of lead 16A. The stimulation and signals may be conducted between the electrodes and IMD 14A by conductors within lead 16A, which are electrically connected to IMD 14A by connectors at proximal end 18A of lead 16A.

In the example of FIG. 1B, system 10B includes an implantable medical device (IMD) 14B configured to deliver therapy to and/or sense physiological signals from target tissue. The target tissue may include or be near spinal cord 28 and/or pelvic nerves 8 (e.g., a pudendal nerve or sacral nerve), or any other nervous or muscle tissue that may be stimulated or from which physiological signals may be sensed of patient 12B through lead 16B. More particularly, IMD 14B may deliver electrical stimulation and sense electrical signals via electrodes of a segmented electrode structure at distal end 20B of lead 16B. The stimulation and signals may be conducted between the electrodes and IMD 14B by conductors within lead 16B, which are electrically connected to IMD 14B by connectors at proximal end 18B of lead 16B. IMD 14B may provide neurostimulation to treat symptoms of patient 12B, such as pain, fecal or urinary incontinence, erectile dysfunction, or other sexual dysfunction.

IMDs 14A and 14B (collectively "IMDs 14") may include electronics and other internal components necessary or desirable for providing the functionality described herein as being associated with the device. In one example, IMDs 14 include processing circuitry, memory, signal generation circuitry, sensing circuitry, telemetry circuitry, and a power source. In general, memory of an IMD 14 may include computer-readable instructions that, when executed by processing circuitry of the IMD, cause it to perform various functions attributed to the device herein. For example, processing circuitry of an IMD 14 may control the signal generation circuitry and sensing circuitry according to instructions and/or data stored on memory to deliver therapy to patient 12, sense physiological signals of the patient, and perform other functions related to treating one or more conditions of the patient with IMD 14.

The signal generation circuitry of IMD 14 may generate electrical stimulation that is delivered to patient 12 via electrodes on one or more leads 16, in order to provide, for example, DBS, spinal cord stimulation, or other neuromodulation (e.g., neurostimulation). The sensing circuitry of IMD 14 may monitor electrical signals from electrodes on leads 16 of IMD 14 in order to monitor electrical activity of the patient, e.g., to monitor electrical signals generated by brain 24, other neurological signals or action potentials, or cardiac signals. Telemetry circuitry of IMD 14 may include any suitable hardware, firmware, software or any combination thereof for communicating with another device, such as programmer 24. Under the control of processing circuitry of IMD 14, the telemetry circuitry may receive downlink telemetry from and send uplink telemetry to programmer 24 with the aid of an antenna, which may be internal and/or external.

Programmer 22 may be a handheld computing device, computer workstation, or networked computing device. Programmer 22 may include electronics and other internal components necessary or desirable for executing the functions associated with the device. In one example, programmer 22 includes processing circuitry and memory, as well as a user interface, telemetry circuitry, and power source.

As shown in FIG. 1A, medical device system 10A includes IMD 14A with lead 16A entering through cranium 26 and implanted within brain 24 of patient 12A to deliver deep brain stimulation (DBS). One or more electrodes of a segmented electrode structure at distal end 20A of lead 16A provide electrical pulses to surrounding anatomical regions of brain 24 in a therapy that may alleviate a condition of patient 12A. In some examples, more than one lead 16A may be implanted within brain 24 of patient 12A to stimulate multiple anatomical regions of the brain.

DBS may be used to treat dysfunctional neuronal activity in the brain which manifests as diseases or disorders such as Huntington's Disease, Parkinson's Disease, or movement disorders. The exact reasons why electrical stimulation therapy is capable of treating such conditions of the brain is unknown, but symptoms of these diseases can be lessened or eliminated with electrical stimulation therapy. Certain anatomical regions of brain 24 are responsible for producing the symptoms of such brain disorders. As one example, stimulating an anatomical region, such as the Substantia Nigra, in brain 24 may reduce the number and magnitude of tremors experienced by patient 12A. Other anatomical regions may include the subthalamic nucleus, globus pallidus interna, ventral intermediate, and zona inserta. Anatomical regions such as these are targeted by the clinician during the implantation of lead 16A. In other words, the clinician may attempt to position the distal portion of lead 16A, including the one or more electrodes, as close to these regions as possible.

Figure 2:
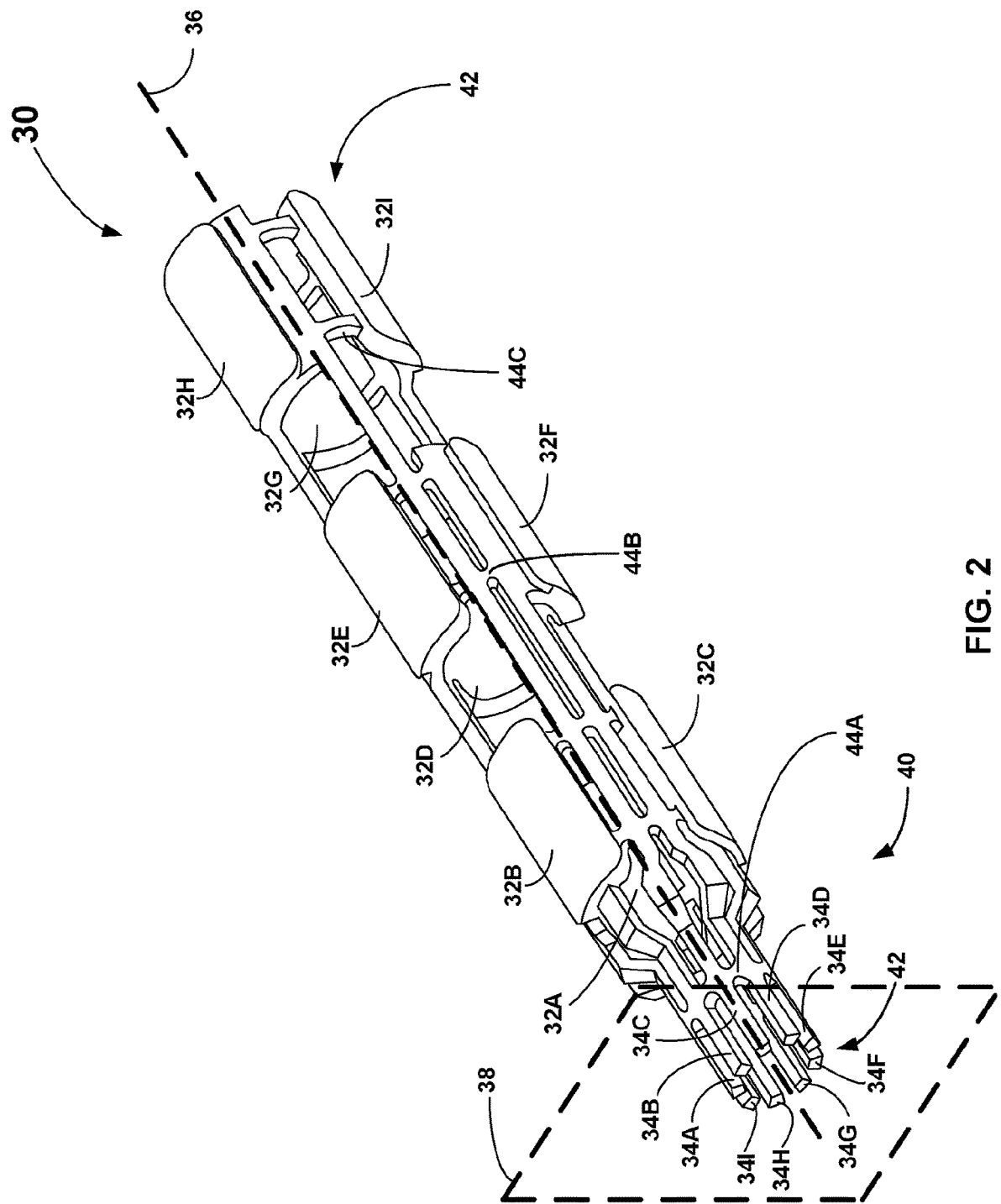
FIG. 2 is a perspective diagram illustrating an example configuration of an implantable segmented electrode structure.

FIG. 2 is a conceptual diagram illustrating an example of an implantable segmented electrode structure 30. The segmented electrode structure 30 may be within the distal portion or distal end 20 of the lead 16, as described in greater detail in FIGS. 3A-3B. As shown in FIGS. 3A-3B, the segmented electrode structure 30 does not need to be arranged at the most distal point on the lead 16, but instead the segmented electrode structure 30 can be configured to axially extend anywhere along a distal portion of the lead 16. In other examples, the segmented electrode structure 30 may be at a proximal portion of the lead 16 (e.g., in such situations where a medical device system 10 is configured to deliver electrical stimulation at a proximal portion of the lead 16). However, for purposes of clarity, segmented electrode structure 30 is discussed predominantly as being configured at a distal portion of the lead 16.

In some examples, the segmented electrode structure is machined from a single piece of conductive material such as titanium, a titanium-tantalum (Ti—Ta) alloy or titanium-molybdenum (e.g., Ti-15% moly). Though the segmented electrode structure 30 of FIG. 2 is depicted as containing exclusively segmented electrodes, it is to be understood that the methods and systems described herein can be used to create electrode structure that comprise any variety of electrodes. For example, some versions of the segmented electrode structure 30 may be comprised of a combination of segmented electrodes and ring electrodes.

The segmented electrode structure 30 includes a plurality of electrode surfaces 32A-I (collectively "electrode surfaces 32"). The electrode surfaces 32 may provide an electrical connection between tissue or organs of a patient 12 and the IMD 14 via a plurality of elongated conductors (e.g., filars) of lead 16. The electrode surfaces 32 are arranged at a plurality of different axial positions and a plurality of different angular positions. In some examples, a plurality of electrode surfaces 32 (e.g., three electrode surfaces 32) share an axial or angular position. For example, as depicted in FIG. 2, electrode surfaces 32A-C are at a first axial position along the longitudinal axis 38 of the segmented electrode structure 30, while electrode surfaces 32D-F are at a second axial position along the longitudinal axis 38, and electrode surfaces 32G-I are at a third axial position along the longitudinal axis 38. Further, as depictured in FIG. 2, electrode surfaces 32B, 32E, and 32H are at a first angular position, while electrode surfaces 32C, 32F, and 32I are at a second angular position, and electrode surfaces 32A, 32D, and 32G are at a third angular position along the segmented electrode structure 30. Other segmented electrode structures 30 may have different arrangements of electrode surfaces 32 at a plurality of axial positions. For example, other segmented electrode structures 30 may have a different number of axial and/or angular positions, and/or other segmented electrode structures 30 may have different numbers of electrode surfaces 32 at respective axial and/or angular positions.

Electrode surfaces 32 may be located at any point along the exterior of the segmented electrode structure 30 to optimize electrical stimulation delivery location. For example, if a therapy requires a high density of electrode surfaces 32 on a distal end 42 of the segmented electrode structure 30, then an axial position closer to the distal end 42 may have relatively more electrode surfaces 32 than an axial position closer to the proximal end 40 of the segmented electrode structure 30. It is to be understood that electrode surfaces 32 of the segmented electrode structure 30 do not need to share either axial positions or angular positions as depicted in FIG. 2. Instead, any number of examples with any number of shared and/or unshared axial and angular positions are contemplated.

The segmented electrode structure 30 includes a plurality of prongs 34A-I (collectively "prongs 34"). Each prong 34 of the plurality of prongs 34 is connected to at least one of the electrode surfaces 32. In some examples, a prong 34 may connect to more than one electrode surfaces 32. The prongs 34 extend axially throughout the segmented electrode structure 30. Each prong 34 of the plurality of prongs 34 may terminate distally at a respective electrode surface 32. For example, within FIG. 2, prong 34B terminates at electrode surfaces 32B, while prong 34C terminates at electrode surface 32H, and prong 34D terminates at electrode surface 32F. Further, each prong 34 may terminate proximally at a terminal plane 38. The terminal plane 38 may be perpendicular to the longitudinal axis 36 that is defined by the segmented electrode structure 30. The plurality of prongs 34 may terminate upon the terminal plane 38 in a circular arrangement 42 as depicted in FIG. 2. The circular arrangement 42 may be centered on the longitudinal axis 36 with a first radius from the longitudinal axis 36. The first radius is discussed in greater detail in FIG. 6A.

In some examples, the electrode surfaces 32 may be arranged at a first radial distance from the longitudinal axis 36 as depicted in FIG. 2. In such examples, the prongs 34 may extend axially throughout the segmented electrode structure 32 at a second radial distance from the longitudinal axis 36. As depicted in FIG. 2, the second radial distance may be shorter than the first radial distance, such that the electrode surfaces 32 are raised relative to the prongs 34 (e.g., the electrode surfaces 32 are radially further from the longitudinal axis 36 than the prongs 34). The first radius of the circular arrangement 42 may be less than the second radial distance as depicted in FIG. 2, such that the plurality of prongs 34 become relatively closer to the longitudinal axis 36 at the proximal end 40 of the segmented electrode structure 30 (e.g., the proximal prongs 34 become closer to the longitudinal axis 36 in comparison to the distance between prongs 34 and the longitudinal axis 36 at the distal end 42 of the segmented electrode structure 30). The first radial distance, second radial distance, and first radius are described in greater detail in the discussion of FIG. 6C.

In some examples, the segmented electrode structure 30 may include a plurality of tabs 44A-C (collectively "tabs 44"). Tabs 44 may maintain the structural integrity of the segmented electrode structure 30. Tabs 44 may connect prongs 34 and/or electrode surfaces 32 of the segmented electrode structure 30 to respective circumferentially adjacent prongs 34 and/or electrode surfaces 32. For example, tab 44A connects prong 34C to prong 34D near the proximal end 40 of the segmented electrode structure 30. For another example, tab 44B also connects prong 34C to prong 34D. For another example, tab 44C connects prong 34C to electrode surface 32I at the distal end 42 of the segmented electrode structure 30. The plurality of tabs 44 may be configured to be removed in conjunction with an overmolding procedure such that each electrical surface 32 of a final segmented electrode structure 30 within a lead 16 only has electrical contact with a single prong 34.

The segmented electrode structure 30 may be configured to receive a non-metallic material to maintain a spaced arrangement of prongs and electrode surfaces relative to each other. This non-metallic material may define a longitudinal lumen of the segmented electrode structure 30. This longitudinal lumen may be configured to receive a lead stylet within the segmented lead structure 30. Alternatively, the non-metallic material may substantially fill a space within the segmented electrode structure 30. In some examples, this non-metallic material includes molding as provided by the overmolding procedure as discussed herein.

FIGS. 3A and 3B are perspective diagrams illustrating an example configuration of the distal end 20 of an implantable medical lead 16 that utilizes a segmented electrode structure 30. FIGS. 3A and 3B depict a distal end 20 of a lead 16 with a segmented electrode structure 30 comprising a plurality of electrodes 32-F and a plurality of prongs 34A-E, an overmold 52, a plurality of elongated conductors 56A-D (collectively "elongated conductors 56"), and an insulator 54 of the plurality of elongated conductors 56. Overmold 52 is adjacent to and surrounds the segmented electrode structure 30. The overmold 52 may provide support to the segmented electrode structure 30 (e.g., support in lieu of the tabs 44) as well as electrical isolation for the electrode surfaces 32. In some examples, the overmold 52 is a hardenable polymeric material that is injected into a mold containing segmented electrode structure 30. Within this mold, the overmold may fill in the interstices of the segmented electrode structure 30. Tabs 44 may be removed from the segmented electrode structure 30 in conjunction with this overmolding procedure as described herein. In some examples, the overmolding procedure may cover the entirety of the lead 16, such that the overmold 52 of the lead is 16 substantially continuous. In other examples, the overmold procedure may be conducted piecemeal to allow for the tabs 44 to be removed, as discussed in greater detail in FIG. 10.

In some examples, after the polymeric material is hardened to create the overmold 52 at the distal end 20 of the lead 16, an exterior portion of the overmold 52 may be trimmed and/or removed to expose the electrode surfaces 32, such that the electrode surfaces 32 may have an electrical connection to patient tissue. In other examples, the outer surfaces of the electrode surfaces 32 may be adjacent to the mold upon the conclusion of the overmolding procedure, such that the outer surfaces of the electrode surfaces 32 remain exposed and require no trimming or removal of overmold material. In some examples, the hardenable organic polymeric material ("overmold material") may be selected from a group consisting of polyurethanes, polyurethanes with surface-modifying end groups, polyurethane silicone block copolymers, silicones, fluoropolymers, fluoroelastomers, polyethylenes, and polyesters. In other words, overmold 52 may keep the exterior of the electrode surfaces 32 exposed while providing support (e.g., support such as the tabs 44 initially provide) and electrical isolation between electrode surfaces 32 and prongs 34 of the segmented electrode structure 30, and protecting the interior of the distal end 20 of the lead 16 from external conditions. In some examples, the overmold 52 may also aid in retaining electrode surfaces 32 and prongs 34 in their respective positions.

In some examples, as depicted in FIG. 3B, no tabs 44 are present in the overmolded segmented electrode structure 30 due to a tab 44 removal procedure. After the tabs 44 are removed, each electrode surface 32 may only have electrical contact with one respective prong 34, which is respectively electrically connected to an IMD 14 through a respective elongated conductor 56.

The elongated conductors 56 in FIG. 3B are a representation of insulated electrical conductors (e.g., wires) coupling the electrode surfaces 32 to an IMD 14. In the example of FIG. 3B, the elongated conductors 56 are within an insulator 54, which provides support and electrical isolation to the elongated conductors 56. In some examples, the elongated conductors 56 may be coiled within the insulator 54 (e.g., coiled co-radially) to form insulated helical conductors. The insulator 54 may terminate where depicted (e.g., at a point where an elongated conductor hub, as discussed in FIG. 4, proximally begins), or the insulator 54 may terminate at a different point within the lead 16. The elongated conductors 56 and insulator 54 may axially extend as depicted in FIG. 3B to the proximal end 18 of the lead 16.

The configuration, type, and number of the elongated conductors 56 is not limited to the example illustrated in FIG. 3B and, in other examples, lead 16 as described in FIGS. 1A-2 may include any configuration, type, and number of conductors. In some examples, one elongated conductor 56 may electrically couple to a plurality of electrode surfaces 32. In the example configuration of FIG. 3B, each electrode surface 32 is electrically connected to one prong 34 which is respectively electrically connected to one elongated conductor 56.

In some examples, the electrode surfaces 32 may be electrically connected to an IMD 14 with a stimulation generation circuitry configured to deliver electrical stimulation via a selected combination of one or more of the electrode surfaces 32. In such examples, electrode surfaces 32 may be electrically connected to the stimulation generation circuitry (e.g., connected via respective elongated conductors 56 and prongs 34). In some examples, electrode surfaces 32 may be electrically connected to an IMD 14 with a sensing circuitry configured to sense electrical signals of a patient via a selected combination of one or more of the electrode surfaces 32. In such examples, electrode surfaces 32 may be electrically connected to the sensing circuitry (e.g., connected via respective elongated conductors 56 and prongs 34). In some examples, the IMD 14 includes both a signal generation circuitry and a sensing circuitry, and each electrode surface 32 may be electrically connected to the signal generation circuitry and sensing circuitry (e.g., connected via respective prongs 34 and elongated conductors 56).

In some examples (not shown), a segmented electrode structure 30 may connect to a plurality of elongated conductors 56 at a proximal portion of the lead 16 rather than or in conjunction with a segmented electrode structure 30 connecting to a plurality of elongated conductors 56 at a distal portion of the lead 16. Such examples may occur in such medical systems 10 where it is desired to deliver electrical stimulation to a proximal portion of the lead 16.

Figure 4:
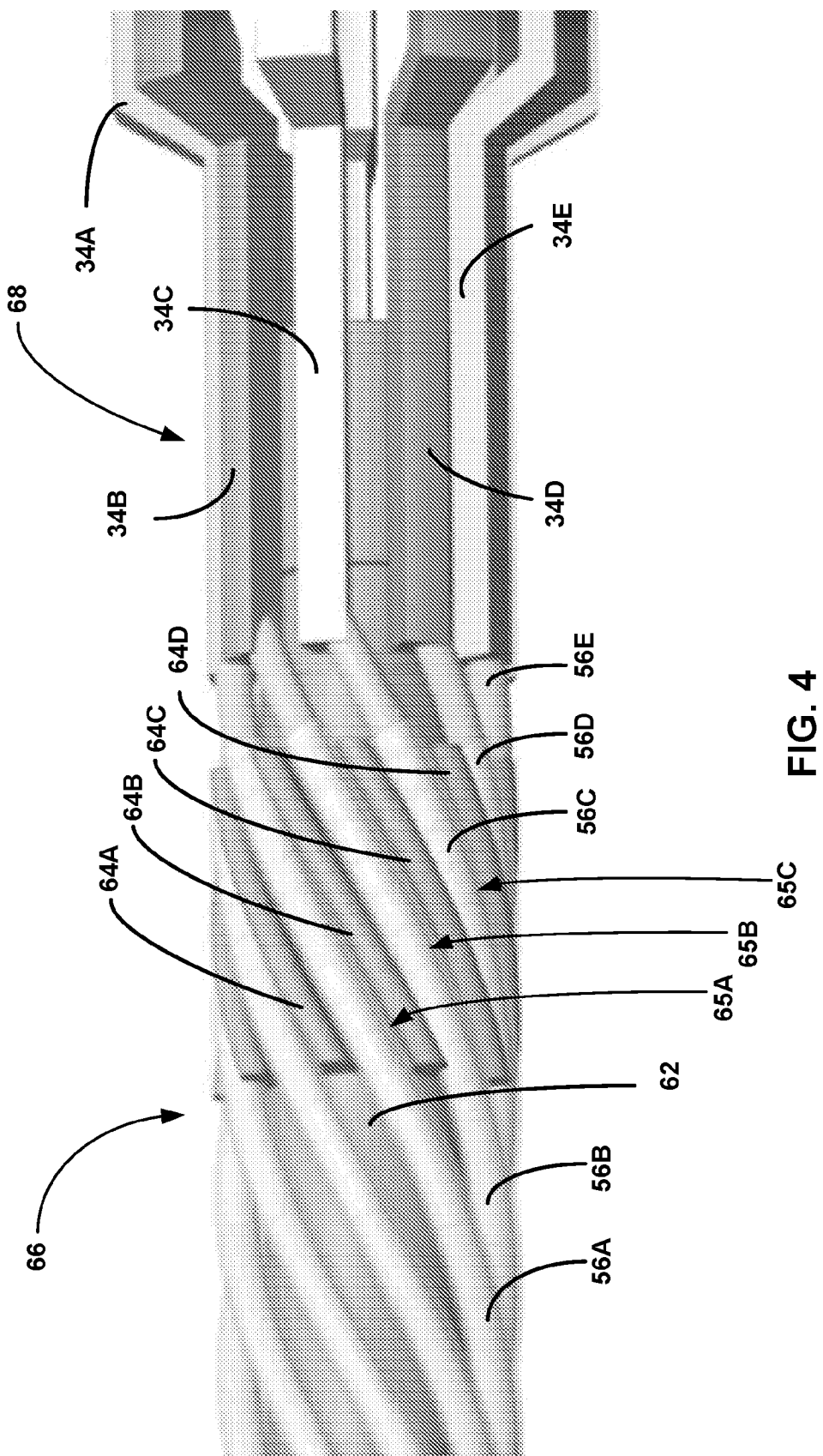
FIG. 4 is a perspective diagram illustrating an example configuration of a plurality of elongated conductors that are electrically connected to a plurality of prongs after the plurality of prongs has received an elongating conductor hub.

FIG. 4 depicts a close-up of an example configuration of a plurality of prongs 34 that have received an elongated conductor hub 62. The elongated conductor hub 62 has a proximal end 66 and a distal end 68. The plurality of prongs 34 is configured to receive the distal portion 68 of the elongated conductor hub 62. In some examples, the prongs 34 receive the distal portion 68 of the elongated conductor hub 62 with a slight interference fit so that the elongated conductor hub 62 stays relatively stable upon being received by the prongs 34.

The proximal portion 66 of the elongated conductor hub 62 may arrange elongated conductors 56 to terminate near respective prongs 34. For example, the elongated conductor hub 62 may arrange elongated conductors 56 such that it is possible to weld respective elongated conductors 56 to respective prongs 34 without any further movement/manipulation of the respective elongated conductors once the prongs 34 have received the elongated conductor hub 62. Arranging the elongated conductors 56 to terminate near the respective prongs 34 without manipulation may allow for automated laser welding of the elongated conductors 56 to the prongs 34.

In some examples, the proximal portion 66 of the elongated conductor hub 62 arranges the elongated conductors 56 with a plurality of helical splines 64A-D (collectively "helical splines 64") of the elongated conductor hub 62. These helical splines 64, as depicted in FIG. 4, extend radially out from the elongated conductor hub 62 to define a plurality of helical channels 65A-C (collectively "helical channels 65"). The helical channels 65 may receive elongated conductors 56. The helical channels 65 may be configured to receive the elongated conductors 56 such that the elongated conductors 56 are uncoiled (e.g., uncoiled from a co-radial coiled configuration in which the elongated conductors 56 extend through the lead 16 within the insulator 54) and straightened to terminate near respective prongs 34 as discussed herein.

For example, as depicted in FIG. 4, elongated conductor 56A is received by the helical channel 65A. The helical channel 65A is defined by the helical splines 64A and 64B. In some examples, the helical channel 65A may receive the elongated conductor 56A with a slight interference fit, such that the elongated conductor 56A will "snap in" to the helical channel 65A and will not slip out unless actively pulled out. The elongated conductor hub 62 is configured to arrange elongated conductor 56A to terminate near prong 34A. As depicted in FIG. 4, elongated conductor 56A is electrically connected (e.g., welded) to prong 34A. In much the same way, elongated conductor 56B is received by a helical channel 65B as defined by helical splines 64B and 64C such that elongated conductor 56B terminated near and is now electrically connected to prong 34B.

Though in FIG. 4 the helical splines 64 and helical channels 65 are not depicted extending to the proximal end of the elongated conductor hub 62 for purposes of clarity, in some examples the helical splines 64 and channels 65 may extend to a proximal end of the elongated conductor hub 62. In other examples, the helical splines 64 and helical channels 65 axially extend near the proximal end of the elongated conductor hub 62. Other configurations of helical splines 64 and channels 65 consistent with this disclosure are also contemplated.

Figure 5:
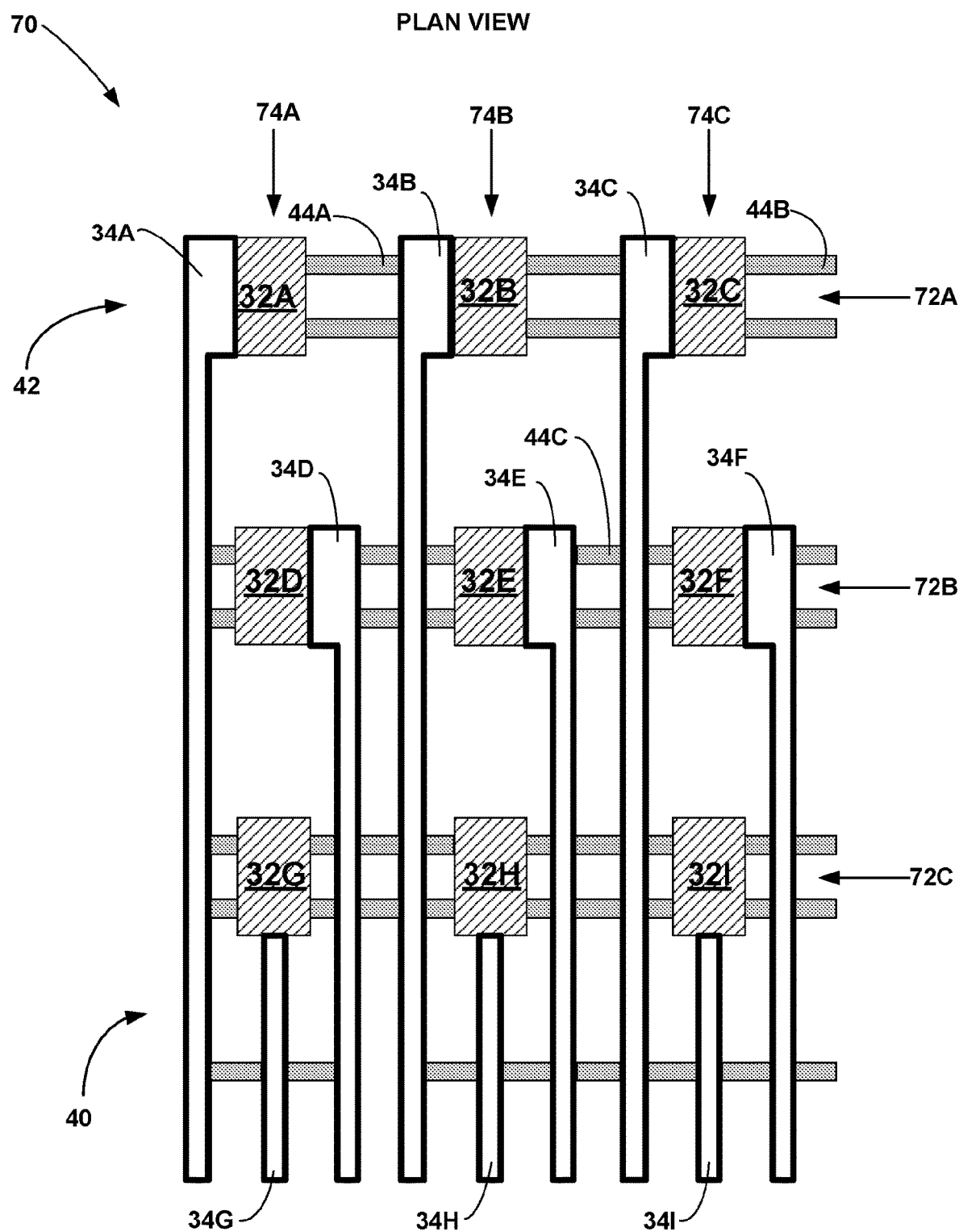
FIG. 5 is a plan diagram illustrating an example configuration of an implantable electrode structure.

FIG. 5 depicts a plan view 70 of an example configuration of a segmented electrode structure 30. The plan view 70 includes a plurality of electrode surfaces 32A-I, prongs 34A-I, and tabs 44A-C. Although plan view 70 depicts each electrode surfaces 32, prong 34, and tab 44 with a different shading for purposes of clarity, it is to be understood that in some examples all electrode surfaces 32, prongs 34, and tabs 44 consist of the same material and comprise a single structure machined from a single source. As is shown within the plan view 70, each prong 34 is electrically connects to a single electrode surface 32. Tabs 44 interconnect circumferentially adjacent prongs 34 and/or electrode surfaces 32 with each other. Tabs may connect electrode surfaces 32 to prongs 34 (e.g., such as tab 44A) or prongs 34 to prongs 34 (e.g., such as tab 44C). In some examples (not depicted) tabs 44 may connect electrode surfaces 32 to electrode surfaces 32. Tabs 44 on the far right of the plan view 70, such as tab 44B on the distal portion 42 of the segmented electrode structure 30, wrap around to connect to the respective far left component, in this case prong 34A.

The electrode surfaces 32 are arranged at a plurality of axial positions 72A-C (collectively "axial positions 72") and a plurality of angular positions 74A-C (collectively "angular positions 74") (e.g., angular as when configured cylindrically rather than in plan view 70). As depicted in the plan view 70, in some examples numerous electrode surfaces are located at a single axial position 72. For example, electrode surfaces 32A-C are all depicted at axial position 72A, while electrode surfaces 32D-F are all depicted at axial position 72B, and electrode surfaces 32G-I are all depicted at axial position 72C. Additionally, as depicted in the plan view 70, electrode surfaces 32 are arranged equidistant apart at each axial position 72, such that each electrode surfaces 32 is centered 120 degrees away (e.g., when constructed in a cylinder around the longitudinal axis 36 of the segmented electrode structure 30) from neighboring electrode surfaces 32 at the same axial position 72. Also, as depicted in the plan view 70, numerous electrode surfaces 32 may be located at a single angular position 74, such as electrode surfaces 32A, 32D, 32G at angular position 74A, electrode surfaces 32B, 32E, 32H at angular position 74B, and electrode surfaces 32C, 32F, 32I at angular position 74C. Different combinations of various amounts of electrode surfaces 32 at different axial positions 72 and/or angular positions 74 are also contemplated.

Figure 6A:
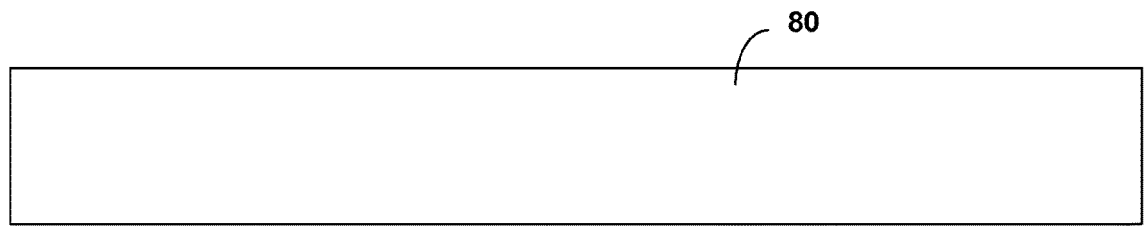
FIGS. 6A-6C are perspective diagrams illustrating an example segment of conductive material from which to machine an intermediate structure, an example configuration of an intermediate structure from which to laser cut an implantable segmented electrode structure, and an example configuration of an implantable segmented electrode structure, respectively.
Figure 6B:
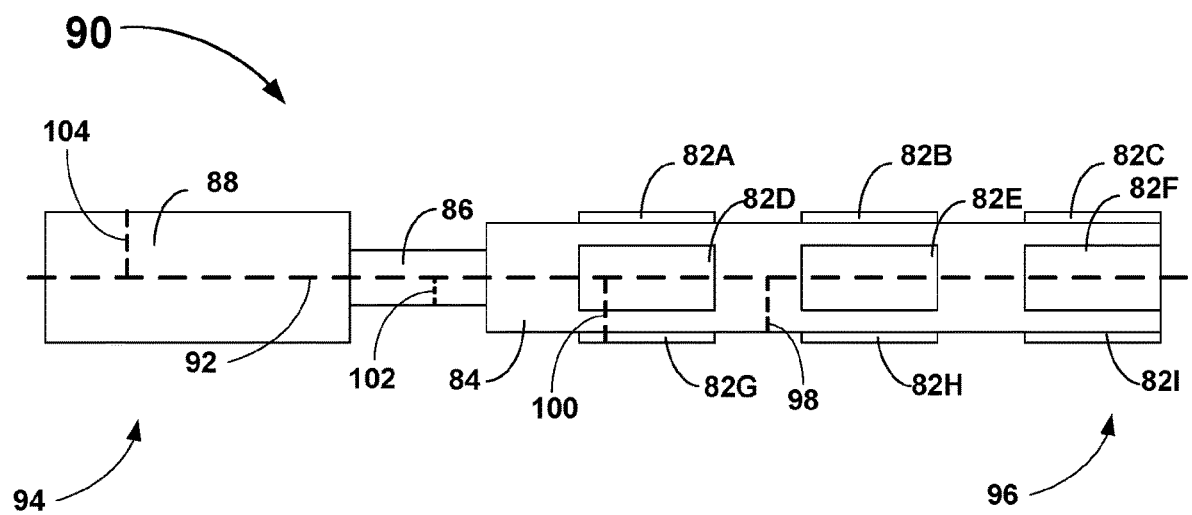
Figure 6C:
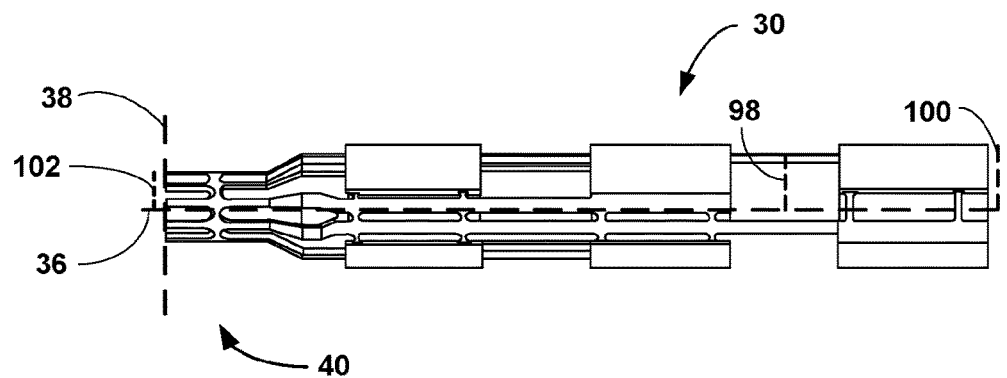

FIGS. 6A-6C depict an example of a three-stage manufacturing process to create a segmented electrode structure 30. FIG. 6A depicts a segment 80 of conductive material. The segment 30 may be a cylinder or a rectangular cuboid. The conductive material may be titanium, a principally titanium alloy, or any other suitable conductive material. The segment may be hollow, substantially hollow (e.g., hollow most of the way through), or solid (e.g., not hollow). The segment 80 is machined to an intermediate structure 90 as depicted in FIG. 6B. The intermediate structure 90 may be hollow. The intermediate structure 90 may be generally cylindrical as defined by a longitudinal axis 92. A distal end 96 of the intermediate structure 90 includes an outer surface 84 at a first radius 98 from the longitudinal axis 92. The distal portion 96 of the intermediate structure 90 also includes a plurality of raised surfaces 82A-I (collectively "raised surfaces 82"). The raised surfaces 82 are raised from (e.g., further away from the longitudinal axis 92 than) the outer surface 84. The raised surfaces 82 have a second radius 100 from the longitudinal axis 92. As depicted in FIG. 6B, the second radius 100 is greater than the first radius 98.

In some examples, the intermediate structure 90 includes a proximal portion 86. The proximal portion 86 may include an outer surface at a third radius 102 from the longitudinal axis 92. As depicted in FIG. 6B, the first radius 98 is greater than the third radius 102. In some examples the intermediate structure 90 further includes a gripping section 88. The gripping section 88 is located at a proximal end 94 of the intermediate structure. The gripping section 88 may be cylindrical. In other examples, the gripping section 88 may be a rectangular cuboid. An outer surface of the gripping section 88 is a fourth radial distance 104 away from the longitudinal axis 92 of the intermediate structure 90. The fourth radial distance 104 is greater than the first radius 98. In some examples, the fourth radial distance is equal to the second radius 100. In other examples, the fourth radial distance is equal to the radius of the initial segment 80 (i.e., the gripping section is not machined as part of the operation of creating the intermediate structure 90 from the segment 80). In certain examples, the gripping section may be the only portion of the intermediate structure 90 that is not hollow.

FIG. 6C depicts a segmented electrode structure 30. The segmented electrode structure 30 may be laser-cut from the intermediate structure 90. As such, in some examples, the segmented electrode structure 30 is a single continuous structure comprising a single conductive material. Laser cutting the intermediate structure 90 into the segmented electrode structure 30 may include removing the gripping section 88. In some examples, the gripping section 88 is used to grip and articulate the intermediate section 90 as the intermediate section 90 is laser-cut into the segmented electrode structure 30. In such examples, the gripping section 88 may be removed (cut off from the proximal end of the segmented electrode structure 30) once the laser-cutting procedure is otherwise complete. In some cases, the gripping section 88 may be removed at the terminal plane 38.

The raised surfaces 82 of the intermediate structure 90 may be left relatively intact during the laser-cutting procedure to become the electrode surfaces 32 of the segmented electrode structure 30. In some examples, the second radius 100 of the raised surfaces 82 is equal to the first radial distance 100 of the electrode surfaces. In certain examples, the raised surfaces 82 of the intermediate structure 90 may undergo small refinement during the laser-cutting procedure, such as receiving chamfers or bevels at various edges.

The outer surface 84 of the distal end 96 of the intermediate structure 90 may be laser-cut into the prongs 34 and tabs 44 of the segmented electrode structure 30. In some examples, the first radius 98 of the outer surface is equal to the second radial distance of the axially-extending prongs 34. In some examples, the proximal portion 86 of the intermediate structure 90 may be cut into the proximal end 40 of the segmented electrode structure 30 that includes the prongs 34 terminating in a circular arrangement at the terminal plane 38. In such examples, the third radius 102 of the proximal portion 86 may be equal to the third radius 102 of the circular arrangement.

Figure 7A:
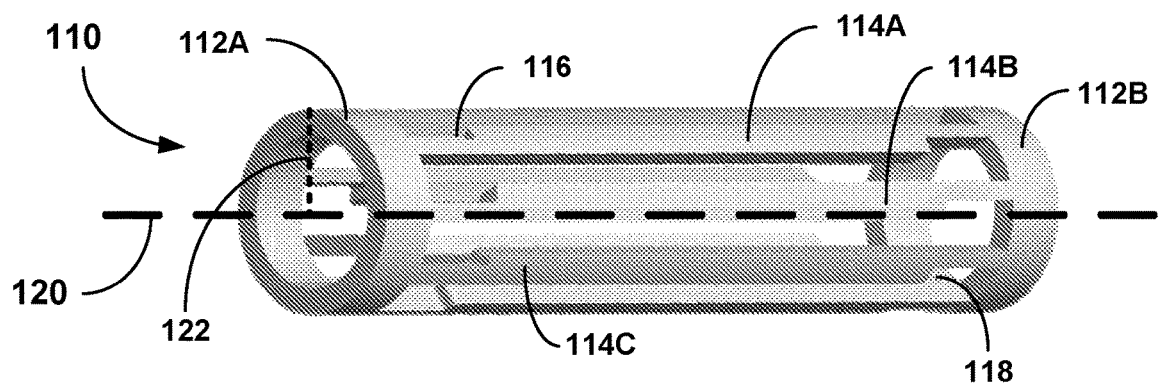
FIGS. 7A-7C are perspective diagrams illustrating example configurations of implantable segmented electrode sub-assemblies.
Figure 7B:
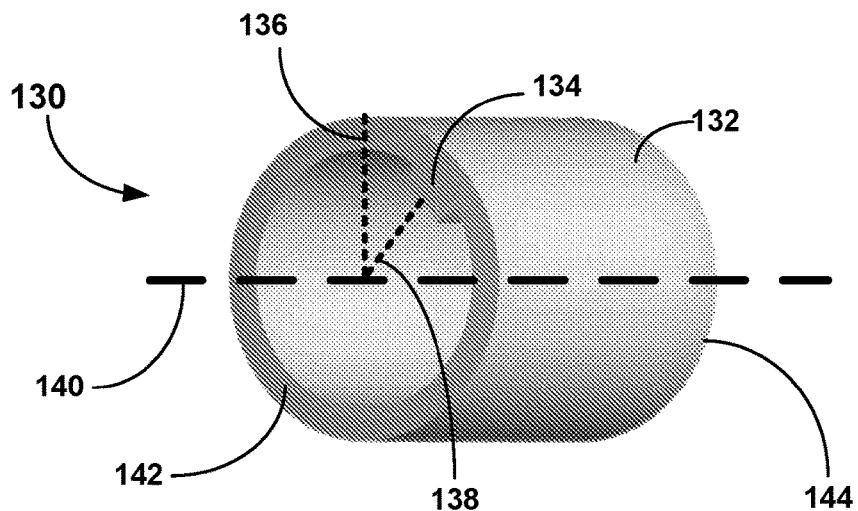
Figure 7C:
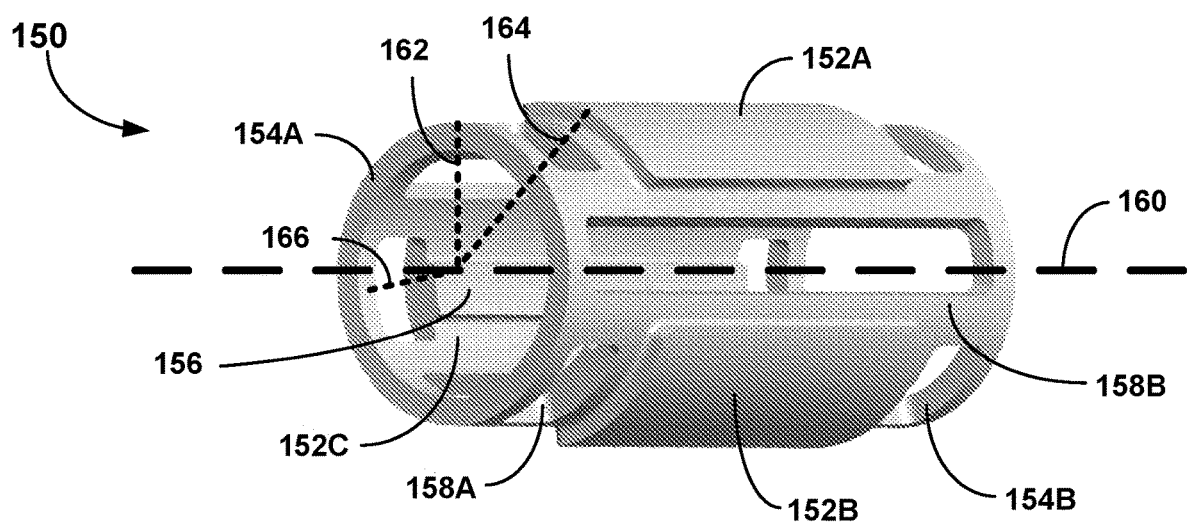

FIGS. 7A-7C depict example configurations of sub-assemblies that may be used to create different versions of implantable segmented electrode structures in some examples. FIG. 7A depicts a prong sub-assembly 110 comprising a plurality of prongs 114A-C (collectively "prongs 114") and two prong retention rings 112A-B (collectively "prong retention rings 112"). The prongs 114 extend axially between a hollow proximal prong retention ring 112A and a hollow distal prong retention ring 112B. The retention rings 112 may maintain the structural integrity of the prongs 114, much the same as how the tabs 44 of the segmented electrode structure 30 maintained the structural integrity of the segmented electrode structure 30 prior to the overmolding procedure. Each prong 114 may have a proximal notch 116 near the proximal prong retention ring 112A and a distal notch 118 near the distal prong retention ring 112B. Proximal notches 116 may be configured to interlock with distal notches 118.

The prongs 114 may extend parallel with a first longitudinal axis 120 defined by the prong sub-assembly 110. Both prong retention rings 112 may be circular in shape and are centered on the first longitudinal axis 120 with a first radius 122. The prongs 114 may extend axially through the prong sub-assembly 110 at a radial distance from the longitudinal axis 120 equal to the first radius 122. In some examples, the prongs 114 are arranged equidistant around the prong retention rings 112 as depicted in FIG. 7A. In other examples the prongs 114 may be clustered with higher density in one or more areas as required by a final segmented electrode assembly.

FIG. 7B depicts a ring electrode subassembly 130 comprising a ring electrode 132 and an interior ridge 134. The ring electrode 132 may be a hollow cylinder that defines a second longitudinal axis 140. The outer surface of the ring electrode 132 may be a second radial distance 136 away from the second longitudinal axis 140. The second radial distance 136 of the ring electrode subassembly 130 is greater than the first radial distance 122 of the prong subassembly 110. The interior ridge 134 may extend radially inward from the interior of the ring electrode 132 towards the second longitudinal axis 140. The inward radial extension of the interior ridge 134 may be defined by a third radial distance 138. The third radial distance may be substantially similar to or slightly greater than the first radial distance 122 of the prong sub-assembly 110. In some examples, the interior ridge 134 extends axially continuously from a proximal end 142 of the ring electrode 132 to a distal end 144 of the ring electrode 132. In other examples, the interior ridge 134 only extends axially for a portion of the ring electrode 132.

FIG. 7C depicts a segmented electrode sub-assembly 150 comprising a plurality of segmented electrode 152A-C (collectively "segmented electrodes 152"), two segmented electrode retention rings 154A-B (collectively "segmented electrode retention rings 154"), and a plurality of connectors 158A-B (collectively "connectors 158"). The segmented electrode sub-assembly 150 defines a third longitudinal axis 160. Connectors 158 may extend axially between a proximal segmented electrode retention ring 154A and a distal segmented electrode retention ring 154B. Connectors 158 may run parallel to the third longitudinal axis 160 at a fourth radial distance 162 from the third longitudinal axis 160. The fourth radial distance 162 may be greater than the first radial distance 122 of the prong sub assembly 110. Both segmented electrode retention rings 154 may be circular and hollow in shape and centered on the third longitudinal axis 160. Both segmented electrode retention rings 154 may have a radius that is equal to the fourth radial distance 162.

Segmented electrodes 152 may be axially located between the two segmented electrode retention rings 154. Segmented electrodes 152 may be angularly positioned around the third longitudinal axis 160. For example, as depicted in FIG. 7C, three segmented electrodes 152 may be arranged equidistant away from each other around a longitudinal axis 160, such that the center of each segmented electrode 152 is rotationally 120 degrees away from the center of the neighboring segmented electrode 152. The exterior surface of each segmented electrode 152 may be cylindrical in shape and centered on the third longitudinal axis 160. Segmented electrodes 152 may be located a fifth radial distance 164 away from the longitudinal axis 160. The fifth radial distance 164 may be substantially similar to the second radial distance 136 of the ring subassembly 130.

Each segmented electrode 152 is connected to both segmented electrode retention rings 154 by two connectors 158. Segmented electrodes 152 may have one connector 158 on either angular side of the respective segmented electrode 152 as depicted in FIG. 7C. For example, segmented electrode 152B is connected to both segmented electrode retention rings 154 by connectors 158A and 158B.

Each segmented electrode 152 may have an interior ridge 156. Interior ridges 156 may extend radially inward from the interior of the segmented electrodes 152 towards the third longitudinal axis 160. The inward radial extension of the interior ridge 156 may be defined by a fifth radial distance 166. The fifth radial distance 166 may be substantially similar to or slightly greater than the first radial distance 122 of the prong sub-assembly 110 and the third radial distance 138 of the ring sub assembly 130. In some examples, the interior ridge 156 extends axially continuously from a proximal end of a segmented electrode 152 to a distal end of a segmented electrode 152. In other examples, the interior ridge 156 only extends axially for a portion of a segmented electrode 156.

Figure 8A:
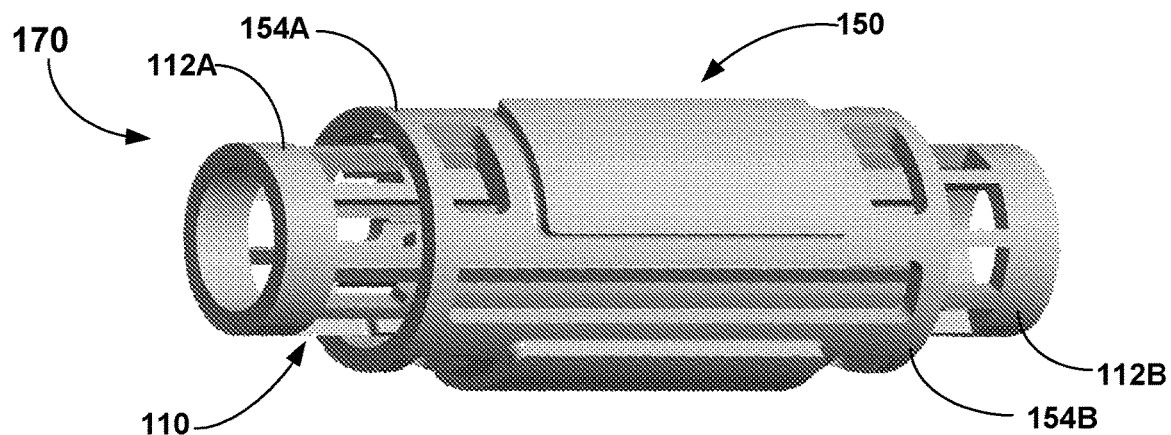
FIGS. 8A-8C are perspective diagrams illustrating example configurations of an implantable segmented electrode structure that uses sub-assemblies in a pre-overmolding stage, a post-overmolding with retention rings stage, and a post-overmolding without retention rings stage, respectively.
Figure 8B:
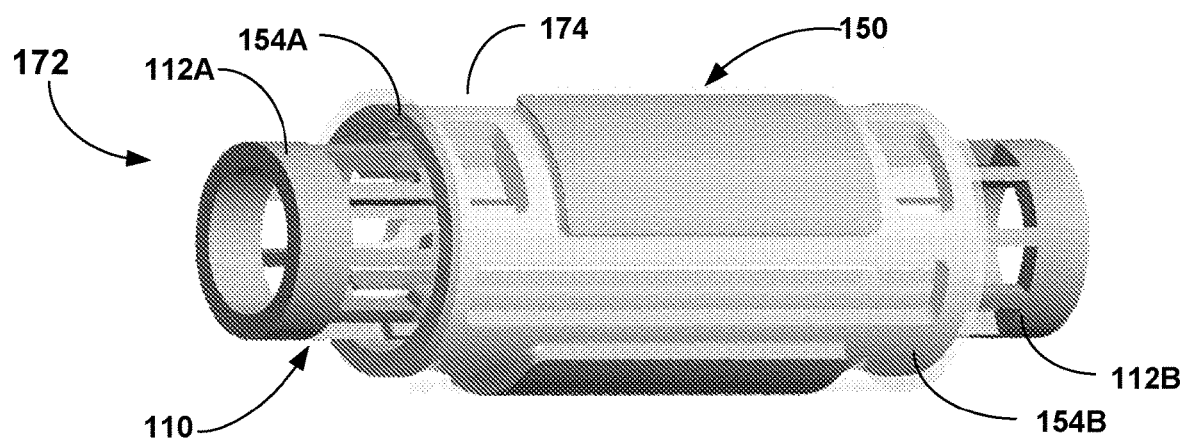
Figure 8C:
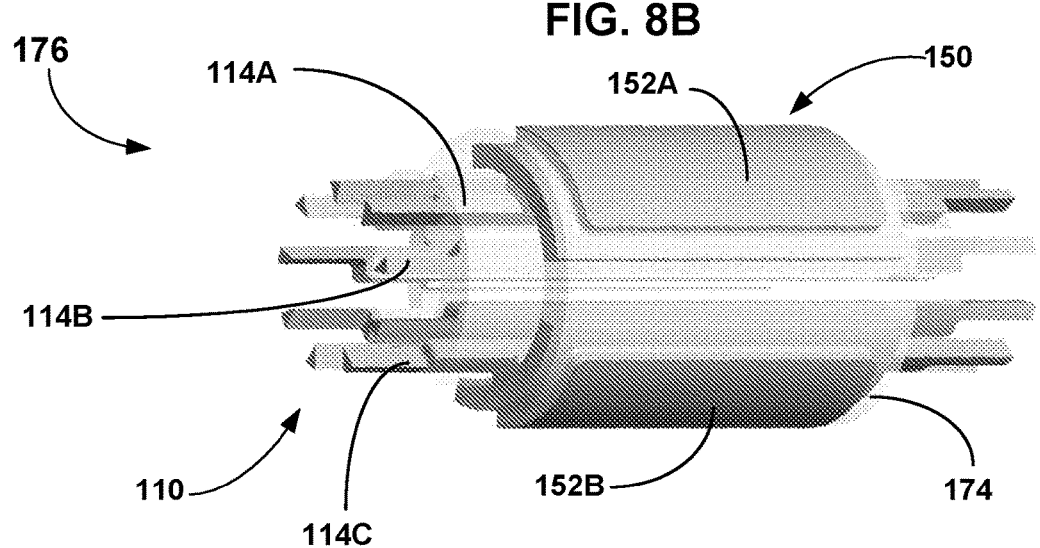

FIGS. 8A-8C depict example stages of a process to create an implantable segmented electrode structure using example subassemblies. FIG. 8A depicts a pre-overmolding segmented electrode assembly 170. The pre-overmolding segmented electrode assembly 170 comprises a segmented electrode subassembly 150 fitted over a prong subassembly 110. Each segmented electrode 152 of the segmented electrode subassembly 150 is electrically connected to one prong 114 of the prong subassembly 110. As is depicted in FIG. 8A, before overmolding, both the segmented electrode subassembly 150 and the prong subassembly 110 retain both sets of respective retention rings 154, 112. In some examples, the inner ridges 156 of the segmented electrode subassembly 150 creates an interference fit with respective prongs 112 of the prong subassembly 110 to create a stable structure and create an electrical connection between respective prongs 112 and segmented electrodes 154. In other examples, the inner ridges 156 of the electrode subassembly 150 are welded to respective prongs 112 of the prong subassembly 110 to create a stable structure and create electrical connections.

FIG. 8B depicts a post-overmolding intermediate segmented electrode assembly 172. The intermediate segmented electrode assembly 172 depicts the electrode assembly after the overmolding procedure and before the removal of the retention rings 112, 154. The overmolding procedure creates a overmold 174 that mostly or completely fills the segmented electrode assembly between the proximal segmented electrode retention ring 154A and the distal segmented electrode retention ring 154B. FIG. 8C depicts a final segmented electrode assembly 176 after retention rings 112, 154 have been removed. Removing retention rings 112, 154 may provide electrical isolation for the final segmented electrode assembly 176 as each segmented electrode 152 is only connected to a single prong 114. For example, as depicted in FIG. 8C, segmented electrode 152A is only electrically connected to prong 114A, while segmented electrode 152B is only electrically connected to prong 114C, while prong 114B is not electrically connected to anything but is still structurally secure as a result of the overmolding.

Final segmented electrode assembly 176 may be connected to a plurality of elongated conductors 56 as described herein. For example, a proximal portion of the exposed prongs 114 of the final segmented electrode assembly 176 may receive an elongated conductor hub 62. The elongated conductor hub 62 may arrange elongated conductors 56 to terminate near respective prongs 114. Once elongated conductors 56 are arranged near respective prongs 114 by the elongated conductor hub 62, respective elongated conductors 56 may be welded to respective prongs 114 of the final segmented electrode assembly 176.

Figure 9:
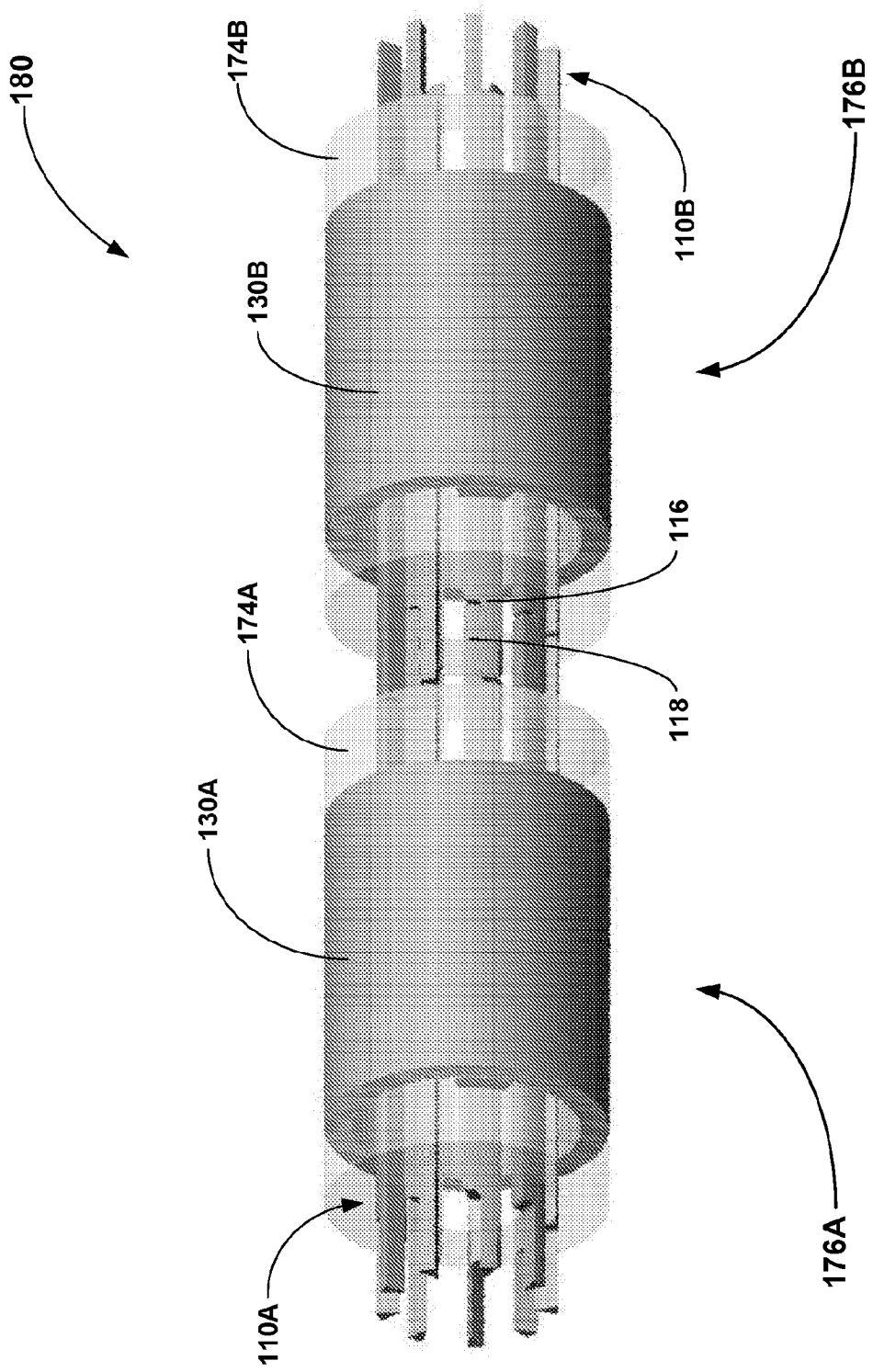
FIG. 9 is a perspective diagram illustrating an example configuration of a daisy-chained implantable segmented electrode structure.

FIG. 9 depicts an example configuration of an example electrode assembly daisy-chain 180 comprising a first segmented electrode assembly 176A daisy-chained to a second segmented electrode assembly 176B. While both segmented electrode assemblies 176A-B (collectively "segmented electrode assemblies 176") are depicted in FIG. 9 with ring sub-assemblies 130A-B rather than segmented electrode sub-assemblies 150 for purposes of simplicity, any correlating form of segmented electrode assembly 176 are applicable and contemplated within an electrode assembly daisy-chain 180. As is shown in FIG. 9, the distal notch 118 of a prong 114 of segmented electrode assembly 176A interlocks with the proximal notch 116 of a prong of segmented electrode assembly 176B. Each interlock pair 118, 116 may be welded together to create an electrical connection between prongs 114 of the first prong subassembly 110A and prongs 114 of the second prong subassembly 110B. In this way, a prong may be connected to an elongated conductor 56 on a proximal end of an electrode assembly daisy-chain 180 and transmit electrical signals through a plurality of prongs 114 of a plurality of prong subassemblies 110 of a plurality of final segmented electrode assemblies 176, potentially delivering an electrical signal to an electrode on a distal end of an electrode assembly daisy-chain 180.

Figure 10:
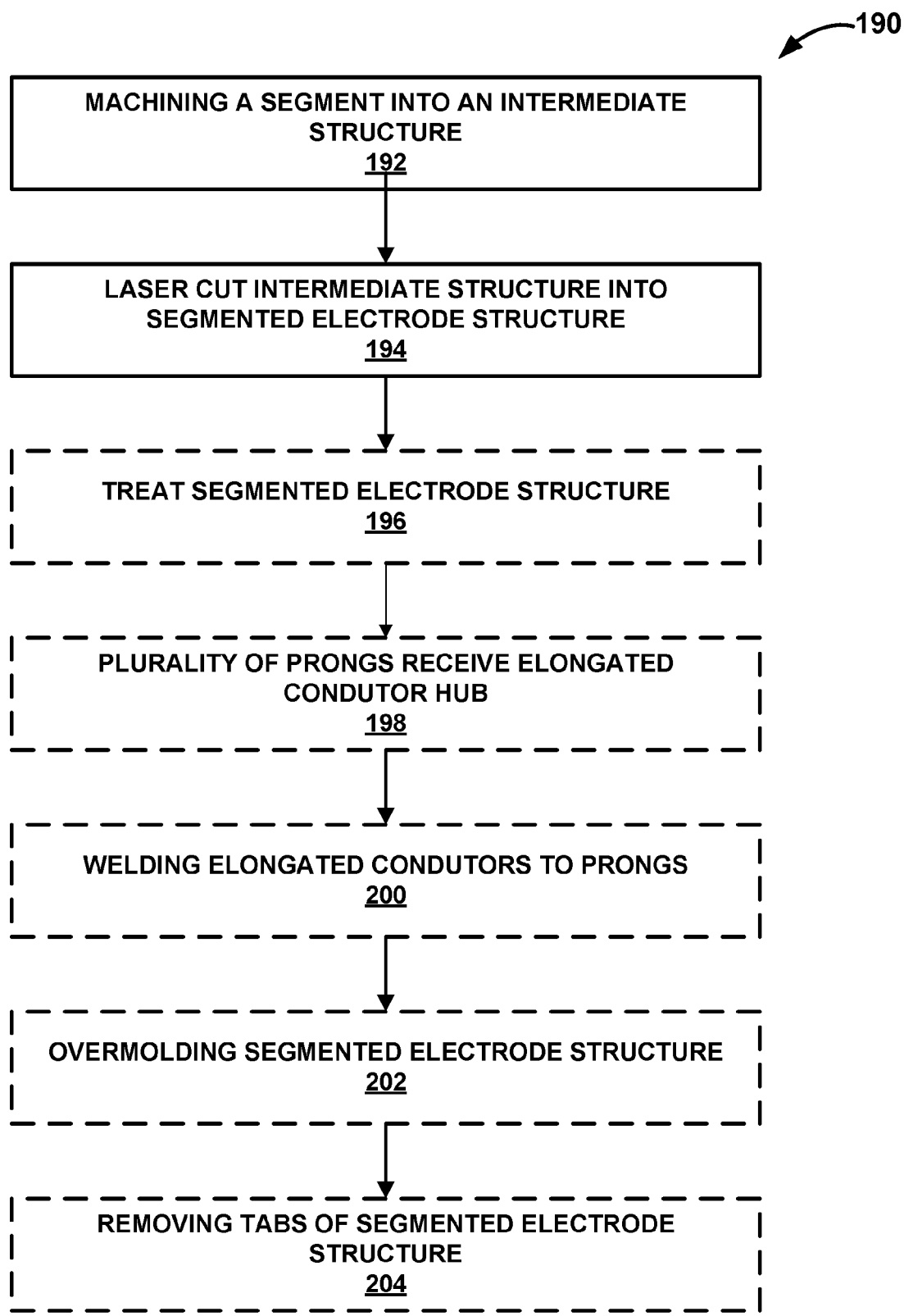
FIG. 10 is an example method of manufacturing an implantable lead using an implantable segmented electrode structure.

FIG. 10 depicts an example method 190 of manufacturing an implantable lead using an implantable segmented electrode structure 30. Dashed boxes of method 190 indicate optional boxes within method 190. The method 190 may be completed using the components and structures described herein.

At block 192 a segment is machined into an intermediate structure. The segment (e.g., segment 80 of FIG. 6A) is a conductive material. The conductive material may be titanium or Ti—Ta or any other appropriate material. The segment may be cylindrical or a rectangular cuboid. In some examples the segment may be solid (e.g., not hollow). The segment may be machined into the intermediate structure using a computer-numeric control (CNC) machine such as a mill and/or a lathe.

The intermediate structure (e.g., the intermediate structure 90 of FIG. 6B) is hollow and cylindrical and defines a longitudinal axis (e.g., longitudinal axis 92). A distal portion of the intermediate structure is machined to include an outer cylindrical surface (e.g., outer surface 84) a first radial distance away (e.g., radial distance 98) from the longitudinal axis. The distal portion of the intermediate structure also includes a plurality of raised surfaces (e.g., raised surface 82). The raised surfaces are raised from the outer surface to a second radial distance away (e.g., radial distance 100) from the longitudinal axis (e.g., where the second radial distance is greater than the first radial distance). The raised surfaces may be at a plurality of axial positions and angular positions along the intermediate structure. The raised surfaces may be cylindrical in shape yet only complete a portion of a radial rotation around the longitudinal axis. For example, in some instances an intermediate structure may have three raised surfaces at a single axial position. These three raised surfaces may be spaced equidistant around the intermediate structure at this axial position, such that the center of each raised surface is rotated 120 degrees around the longitudinal axis away from the center(s) of the next closest raised surface(s).

In some examples, machining the segment into the intermediate structure may include machining a proximal portion (e.g., proximal portion 86) of the intermediate structure. The proximal portion may be hollow and cylindrical. The outer surface of the proximal portion may be a third radial distance (e.g., radial distance 102) away from the longitudinal axis. The third radial distance may be smaller than the first radial distance.

In some examples, the intermediate structure may include a gripping section (e.g., gripping section 88) at a proximal end of the intermediate structure. The gripping section may be used by a CNC machine to grip the segment while machining the segment into the intermediate structure. As such, in some examples the gripping section may be an unmodified portion of the initial segment (e.g., unmodified by the machining of block 192). Alternatively, in some examples the gripping section may be used in block 194 to grip the intermediate section. As such, in these examples the gripping section may be modified from the initial segment.

At block 194 the intermediate structure is laser-cut into an implantable segmented electrode structure (e.g., segmented electrode structure 30 of FIG. 2). As such, the segmented electrode structure may be a unitary structure from a single piece of a material. Laser cutting the intermediate structure into the segmented electrode structure includes cutting the outer surface of the intermediate structure into a plurality of prongs (e.g., prongs 34) that extend axially throughout the segmented electrode structure. The segmented electrode structure includes a plurality of electrode surfaces (e.g., electrode surfaces 32) at a plurality of axial and angular positions. In some examples, the raised surfaces of the intermediate structure are substantially the same as the electrode surfaces of the segmented electrode structure, such that the raised surfaces are minimally modified (or not modified at all) as part of block 194 to create the electrode surfaces.

Laser cutting the outer surface may include leaving a plurality of tabs (e.g., tabs 44) from the outer surface between circumferentially adjacent components. Tabs may connect prongs and/or electrode surfaces to circumferentially adjacent prongs/electrode surfaces. Tabs may provide structural integrity for the segmented electrode structure. In alternative examples, non-conductive tabs may be injected in conjunction with a block 194. These non-conductive tabs may maintain the structure integrity of the segmented electrode structure while maintaining electrical isolation between electrode surfaces.

The laser cutting process may also include removing the gripping section. In some examples, the gripping section may be removed at a proximal terminal plane (e.g., terminal plane 38) of the segmented electrode structure. The gripping section may be gripped by a laser cutting machine to cut the segmented intermediate structure, and then the segmented intermediate structure may be gripped to remove the gripping section. In some examples the gripping section is removed via laser-cutting, while in other examples the gripping section is removed using other means.

In some examples, the outer surface may be laser-cut such that each prong terminates at a respective electrode surface. Further, in some examples, laser cutting the intermediate structure into the segmented electrode structure includes laser cutting prongs that terminate at the terminal plane in a circular arrangement. In certain examples the proximal end of the segmented electrode structure (e.g., the termination of the prongs in the circular arrangement) may be cut from the proximal portion of the intermediate structure. In examples where the prongs proximally terminate at a smaller radial distance from the longitudinal axis than the radial distance at which the prongs connect to the electrode surfaces at the distal end of the segmented electrode structure, laser cutting the segmented electrode structure may include cutting a transition for each prong from the distal radial distance to the relatively smaller proximal radial distance.

At block 196 the segmented electrode structure may be treated. Treating the segmented electrode structure may include cladding, sputtering, or plating the segmented electrode structure to improve the ability of the electrode surfaces to provide electrical stimulation to tissue of a patient. The segmented electrode structure may be treated with platinum, platinum-iridium, titanium-nitride, or other compounds. Additionally, treating the segmented electrode structure may include laser-texturing the segmented electrode structure. In certain examples, only the electrode surfaces of the segmented electrode structure are treated.

At block 198 prongs at the proximal end of the segmented electrode structure may receive an elongated conductor hub (e.g., elongated conductor hub 62 of FIG. 4). In some examples the plurality of prongs may be configured to have a slight interference fit with the elongated conductor hub to stabilize the pairing of the segmented electrode structure and the elongated conductor hub. The elongated conductor hub has a plurality of helical splines (e.g., helical splines 64) that define a plurality of helical channels (e.g., helical channels 65). The helical channels may arrange elongated conductors (e.g., elongated conductors 56) to uncoil and terminate hear respective prongs. At block 200 elongated conductors are welded to respective prongs. Elongated conductors may be laser welded to respective prongs. The elongated conductor hub may arrange the elongated conductors such that no manipulation of the elongated conductors is necessary before elongated conductors can be welded to respective prongs after the elongated conductor hub has been received by the plurality of prongs. The lack of required manipulation may allow automated welding of elongated conductors to respective prongs.

At block 202 the segmented electrode structure undergoes an overmolding procedure. The overmold (e.g., overmold 52 of FIG. 3B) may fill in the hollow portion of the segmented electrode structure. The overmold may act as an electrical insulator between the electrode surfaces of the segmented electrode structure. Eliminating the possibilities of elongated conductors between electrodes within the distal end of the lead (e.g., lead 16 of FIGS. 1A and 1B) using the segmented electrode structure may provide superior electrical insulation and eliminate some electrical cross-talk. At block 204 the tabs are removed. In some examples, the tabs are removed after a partial overmolding procedure covers electrode surfaces and provides structural integrity for the segmented electrode surface while keeping tabs exposed, similar to how retaining rings 112, 154 were left exposed after a partial overmolding in FIG. 8B. After such a "first shot" overmolding procedure provides structural integrity to allow for the removal of the tabs, a second overmolding procedure may provide an overmold for the remaining portions of the segmented electrode structure to complete the overmolding procedure (e.g., resulting in a distal end of a lead as shown in FIG. 3B).

Various examples of the disclosure have been described. These and other examples are within the scope of the following claims.

The invention claimed is:

1. An implantable segmented electrode structure configured to conduct electrical signals between a plurality of elongated conductors of an implantable medical lead and tissue of a patient, the implantable segmented electrode structure comprising:
a plurality of separate electrode surfaces at a plurality of different axial positions and a plurality of different angular positions, wherein each separate electrode surface of the plurality of separate electrode surfaces comprises a respective one of a plurality of prongs extending from the separate electrode surface, and wherein each separate electrode surface of the plurality of separate electrode surfaces and the respective prong of the plurality of prongs are formed as a unitary structure from a piece of a material; and
the plurality of prongs, wherein each prong of the plurality of prongs is electrically connected to the respective one of the plurality of separate electrode surfaces and configured to electrically connect to a respective one of the plurality of elongated conductors, wherein each prong of the plurality of prongs extends axially through the implantable segmented electrode structure and to a proximal end of the implantable segmented electrode structure.

2. The implantable segmented electrode structure of claim 1, wherein each prong of the plurality of prongs distally terminates at the respective separate electrode surface.

3. The implantable segmented electrode structure of claim 1, wherein:
separate electrode surfaces of the plurality of separate electrode surfaces are arranged at a first radial distance from a longitudinal axis of the implantable segmented electrode structure;
the plurality of prongs extends axially through the implantable segmented electrode structure at a second radial distance from the longitudinal axis; and
the second radial distance is less than the first radial distance.

4. The implantable segmented electrode structure of claim 1, wherein the plurality of prongs terminate at a terminal plane at the proximal end of the implantable segmented electrode structure, wherein the terminal plane is substantially perpendicular to the longitudinal axis defined by the implantable segmented electrode structure, and wherein the plurality of prongs terminate in a circular arrangement on the terminal plane.

5. The implantable segmented electrode structure of claim 4, wherein the circular arrangement has a first radius that is substantially centered on the longitudinal axis and is less than the second radial distance.

6. The implantable segmented electrode structure of claim 1, further comprising an elongated conductor hub comprising a proximal portion and a distal portion, wherein the plurality of prongs is arranged to receive the distal portion of the elongated conductor hub, wherein the proximal portion of the elongated conductor hub arranges each of the elongated conductors of the plurality of elongated conductors to terminate near the respective prong of the plurality of prongs.

7. The implantable segmented electrode structure of claim 6, wherein the proximal portion of the elongated conductor hub comprises a plurality of helical splines that define a plurality of helical channels, each channel of the plurality of channels configured to receive a respective conductor of the plurality of conductors.

8. The implantable segmented electrode structure of claim 1, further comprising a plurality of tabs, each of the plurality of tabs connecting one of the plurality of prongs or the plurality of separate electrode surfaces with a circumferentially adjacent other of the plurality of prongs or the plurality of separate electrode surfaces to maintain the structural integrity of the implantable segmented electrode structure.

9. The implantable segmented electrode structure of claim 1, wherein the plurality of tabs includes tabs at different axial positions.

10. The implantable segmented electrode structure of claim 8, wherein the tabs are configured to be removed subsequent to a molding procedure, such that each prong only contacts one respective electrode surface of the implantable segmented electrode structure after all tabs are removed.

11. The implantable segmented electrode structure of claim 1, wherein each prong of the plurality of prongs is configured to be welded to the respective one of the plurality of elongated conductors.

12. The implantable segmented electrode structure of claim 1, wherein the separate electrode surfaces and the prongs are metallic, further comprising a non-metallic material configured to maintain a spaced arrangement of the plurality of separate electrode surfaces and the plurality of prongs relative to each other.

13. A method of creating an implantable segmented electrode structure, the method comprising:
- machining a solid segment of conductive material into a hollow, cylindrical intermediate structure defining the longitudinal axis, wherein a distal portion of the intermediate structure includes an outer surface at a first radius from a longitudinal axis of the intermediate structure and a plurality of raised surfaces at a second radius from the longitudinal axis, wherein the second radius is greater than the first radius; and
- laser cutting the intermediate structure into the implantable segmented electrode structure, wherein the implantable segmented electrode structure comprises:
  - a plurality of separate electrode surfaces at a plurality of different axial positions and a plurality of different angular positions, wherein each separate electrode surface of the plurality of separate electrode surfaces comprises a respective one of a plurality of prongs extending from the separate electrode surface; and
  - the plurality of prongs, wherein each prong of the plurality of prongs is electrically connected to and integral with the respective one of the plurality of separate electrode surfaces and configured to electrically connect to a respective one of the plurality of elongated conductors, wherein each prong of the plurality of prongs extends axially through the implantable segmented electrode structure and to a proximal end of the implantable segmented electrode structure.

14. An implantable medical lead comprising:
- an implantable segmented electrode structure comprising:
  - a plurality of separate electrode surfaces at a plurality of different axial positions and a plurality of different angular positions, wherein each separate electrode surface of the plurality of separate electrode surfaces comprises a respective one of a plurality of prongs extending from the separate electrode surface, and wherein each separate electrode surface of the plurality of separate electrode surfaces and the respective prong of the plurality of prongs are formed as a unitary structure from a piece of a material; and
  - the plurality of prongs, wherein each prong of the plurality of prongs is electrically connected to the respective one of the plurality of separate electrode surfaces and configured to electrically connect to a respective one of the plurality of elongated conductors, wherein each prong of the plurality of prongs extends axially through the implantable segmented electrode structure and to a proximal end of the implantable segmented electrode structure; and
- the plurality of elongated conductors, wherein the plurality of elongated conductors are configured to conduct electrical signals between a medical device and patient tissue via the plurality of separate electrode surfaces of the implantable segmented electrode structure.

\* \* \* \* \*